(12) United States Patent
Dimino et al.

(10) Patent No.: US 11,135,442 B1
(45) Date of Patent: Oct. 5, 2021

(54) INDUCTIVE APPLICATOR COIL ARRANGEMENT FOR THERAPEUTICALLY TREATING HUMAN AND ANIMAL BODIES

(71) Applicant: AAH HOLDINGS LLC, Pinehurst, NC (US)

(72) Inventors: André A. Dimino, Woodcliff Lake, NJ (US); Matthew Drummer, Fort Lee, NJ (US); Junior Pusey, Dumont, NJ (US); Hector Torres, Palisades, NY (US); Francis J. Russo, Glen Head, NY (US)

(73) Assignee: AAH HOLDINGS LLC, Pinehurst, NC (US)

( * ) Notice: Subject to any disclaimer, the term of this patent is extended or adjusted under 35 U.S.C. 154(b) by 0 days.

(21) Appl. No.: 17/279,021

(22) PCT Filed: Oct. 17, 2019

(86) PCT No.: PCT/US2019/056736
§ 371 (c)(1),
(2) Date: Mar. 23, 2021

(87) PCT Pub. No.: WO2020/081813
PCT Pub. Date: Apr. 23, 2020

Related U.S. Application Data

(60) Provisional application No. 62/747,446, filed on Oct. 18, 2018.

(51) Int. Cl.
*A61N 2/02* (2006.01)
*A61N 1/40* (2006.01)

(52) U.S. Cl.
CPC ............... *A61N 2/02* (2013.01); *A61N 1/40* (2013.01)

(58) Field of Classification Search
CPC . A61N 2/02; A61N 1/40; A61N 2/002; A61N 1/0484; A61B 18/18;
(Continued)

(56) References Cited

U.S. PATENT DOCUMENTS 7,740,574 B2   6/2010   Pilla et al.
7,744,524 B2   6/2010   Pilla
(Continued)

FOREIGN PATENT DOCUMENTS

WO   2015161063 A1   10/2015

OTHER PUBLICATIONS

International Search Report and Written Opinion dated Jan. 16, 2020 from PCT International Appln No. PCT/US2019/056736.

*Primary Examiner* — Navin Natnithithadha
*Assistant Examiner* — Sunita Reddy
(74) *Attorney, Agent, or Firm* — Amster, Rothstein & Ebenstein LLP

(57) ABSTRACT

An apparatus for providing pulsed electromagnetic field (PEMF) treatment that comprises an enclosure; one or more first electrically-conductive loops connected to one or more corresponding signal generators configured to generate one or more PEMF signals at the one or more first electrically-conductive loops; one or more second electrically-conductive loops each connected to a respective tunable non-active circuit, the one or more second electrically-conductive loops being arranged at a predetermined distance from the one or more first electrically-conductive loops within the enclosure to form an array, each tunable non-active circuit having at least one variable capacitor for tuning each of the one or more second electrically-conductive loops to the one or more PEMF signals.

20 Claims, 12 Drawing Sheets

(58) Field of Classification Search
CPC .. A41D 13/1236; A41D 2400/32; A47G 9/00;
A47G 9/10; G06K 19/0723
USPC ....................................................... 600/9–15
See application file for complete search history.

(56) References Cited

U.S. PATENT DOCUMENTS

| | | |
|---|---|---|
| 7,758,490 B2 | 7/2010 | Pilla et al. |
| 7,896,797 B2 | 3/2011 | Pilla et al. |
| 8,343,027 B1 | 1/2013 | DiMino et al. |
| 8,415,123 B2 | 4/2013 | Pilla et al. |
| 8,961,385 B2 | 2/2015 | Pilla et al. |
| 9,320,913 B2 | 4/2016 | DiMino et al. |
| 9,415,233 B2 | 8/2016 | Pilla et al. |
| 9,433,797 B2 | 9/2016 | Pilla et al. |
| 10,350,428 B2 | 7/2019 | Pilla |
| 2011/0112352 A1* | 5/2011 | Pilla .................... A61N 1/40 600/14 |
| 2012/0302821 A1* | 11/2012 | Burnett ................ A61N 2/008 600/14 |
| 2013/0158634 A1 | 6/2013 | Edoute et al. |
| 2013/0267943 A1 | 10/2013 | Hancock |
| 2014/0249355 A1* | 9/2014 | Martinez .............. A61N 2/02 600/14 |
| 2015/0080637 A1* | 3/2015 | Bonmassar ........... A61N 2/006 600/14 |
| 2015/0297910 A1* | 10/2015 | Dimino ............. A41D 13/1245 600/14 |

* cited by examiner

INDUCTIVE APPLICATOR COIL ARRANGEMENT FOR THERAPEUTICALLY TREATING HUMAN AND ANIMAL BODIES

CROSS-REFERENCE TO RELATED APPLICATIONS

The present application is a U.S. national stage entry under 35 U.S.C. § 371 of PCT International Patent Application No. PCT/US2019/056736, filed on Oct. 17, 2019, which claims the benefit of and priority to U.S. Provisional Patent Application No. 62/747,446, filed on Oct. 18, 2018, the entire contents of each of which are incorporated by reference herein.

FIELD

The invention relates to an apparatus and method for efficient distribution of pulsed electromagnetic waveforms for targeted pulsed electromagnetic field (PEMF) treatment of living humans and animals, tissues and cells utilizing a combination of active and non-active coils.

BACKGROUND

This apparatus and method relates to the more efficient treatment of living humans, animals, tissues, cells and/or organs by altering their interaction with their electromagnetic environment. The invention also relates to a method of modification of cellular and tissue growth, repair, maintenance, and general behavior by the application of encoded electromagnetic information. More particularly, this invention provides for the application, by surgically non-invasive reactive coupling, of highly specific electromagnetic signal patterns to one or more body parts through an arrangement of active coils inductively coupled to non-active coils upon or within a surface where a human or animal would lie upon or coupled within a garment, bandage or other carrier to apply the output of the inductive coil arrangement to a body, area or part.

SUMMARY

The present invention relates to the use of lightweight flexible active coils that are energized with specific electromagnetic waveforms which may be placed within a mattress, pad, cushioned or non-cushioned substrate to provide application of the therapeutic output while the human or animal is lying thereupon or while a pad, mat, blanket, or the like, incorporating the coils is placed on the human or animal subject. In addition, the inductive coil arrangement can be placed in an appropriate garment, bandage or dressing to deliver the optimum dose of non-invasive pulsed electromagnetic treatment for enhanced repair and growth of living tissue in humans and animals. For example, U.S. Pat. Nos. 7,744,524, 7,740,574, 7,758,490, 7,896,797, 8,343,027, 8,415,123, 8,961,385, 9,320,913, 9,415,233, 9,433,797, and 10,350,428, which are incorporated herein by reference, describe various PEMF apparatuses and corresponding regimens for treating in vivo tissue. Multiple active and non-active coil arrangements are envisaged to provide increased area of coverage. Multiple coil arrangements may be simultaneously or sequentially driven with the same or different waveforms. This beneficial method operates to selectively change the bioelectromagnetic environment associated with the cellular and tissue environment through the use of electromagnetic means such as PRF (pulse repetition frequency) generators and applicator heads therefore as are known in the art.

The inventive method more particularly includes the provision of a flux path, to an entire human or animal body by incorporating one or more inductive coil arrangements within a surface upon which an animal or human may lie upon during treatment. One or more inductive coil arrangements can be applied to provide a flux path to a selectable body region, of a succession of EMF pulses having a minimum width characteristic of at least 0.01 microseconds in a pulse burst envelope having between 100 and 10,000 pulses per burst, in which a voltage amplitude envelope of said pulse burst is defined by a randomly varying parameter in which the instantaneous minimum amplitude thereof is not smaller than the maximum amplitude thereof by a factor of one ten thousandth. Further, the repetition rate of such pulse bursts may vary from 0.01 to 1,000 Hertz. In special cases a mathematically definable parameter may be employed in lieu of said random amplitude envelope of the pulse bursts.

It is, accordingly, an object of the invention to provide an improved electromagnetic method of the beneficial treatment of living human and animal bodies, cells, tissue and organs by proscribing an area circumscribed by the combination of active and non-active coils arranged within a mattress, pad, cushioned or non-cushioned surface upon which an animal or human would lie upon thereby allowing for treatment of the entire body or parts thereof while the human or animal is lying upon such surface.

It is a further object of the invention to provide a unique method of delivery of the improved electromagnetic method by employing a larger surface area without the need to apply energy to each coil in the surface, but in the use of a combination of one or more active coils that would inductively couple with non-active coils that would be configured to be charged with the electromagnetic output from the active coils. The combination and arrangement of active and non-active coils allows for the treatment of larger areas by situating an active coil to be inductively coupled with one or more non-active coils thereby disbursing the energy from the active coil across the areas of the adjacent non-active coils.

It is a further object of this invention that the active coil is powered by an electronic generator that produces the desired EMF signal and applies it to the active coil.

It is another object of this invention that the non-active coils duplicate the output signal from the active coil to act simultaneously as a receiver and transmitter without requiring electrical power by such non-active coils by being inductively coupled to the active coils with a tuned circuit adjusted to the active coil output parameters.

It is a further object to provide a combination of flexible, lightweight active and non-active coils which focus the EMF signal to affected body areas by incorporation in ergonomic support garments.

It is another object to provide an electromagnetic treatment method of the above type having a broad-band, high spectral density electromagnetic field.

It is a further object of the invention to provide a method of the above type in which amplitude and burst duration modulation of the pulse burst envelope of the electromagnetic signal will provide optimal coupling with a maximum number of relevant EMF-sensitive pathways in cells or tissues.

It is yet a further object of the invention to utilize conductive thread to create active and non-active coil arrangements incorporated in daily wear, exercise and sports garments with integrated coils placed according to the desired anatomical target.

It is yet a further object of the invention to utilize a combination of active and non-active lightweight flexible coils or conductive thread to deliver the EMF signal to affected tissue by incorporating such coils or conductive threads as an integral part of various types of bandages, including, but not limited to, compression, elastic, cold or hot compress, etc.

It is another object of the invention to employ several combinations of active and non-active coils which increase the coverage area.

It is another object of the invention to supply the same or different waveforms simultaneously or sequentially to single or multiple inductive coils arrangements.

It is another object of the present invention to construct the inductive coil apparatus for easy attachment to dressings, garments and supports via the use of hook and loop (Velcro®), adhesive or other such temporary attachment means.

It is another object of the invention to provide an improved method of increasing blood flow to affected tissues by modulating angiogenesis.

It is another object of the invention to provide an improved method of increasing blood flow in cardiovascular diseases by modulating angiogenesis.

It is another object of the invention to provide beneficial physiological effects through improvement of micro-vascular blood perfusion and reduced transudation.

It is another object of the invention to provide an improved method of treatment of maladies of the bone and other hard tissue.

It is a still further object of the invention to provide an improved means of the treatment of edema and swelling of soft tissue.

It is another object to provide a means of repair of damaged soft tissue.

It is yet another object to provide a means of increasing blood flow to damaged tissue by modulation of vasodilation and stimulating neovascularization.

It is a yet further object to provide apparatus for use of an electromagnetic method of the character indicated, wherein operation of the apparatus can proceed at reduced power levels as compared to those of related methods known in electromedicine, with attendant benefits of safety, economics, portability, and reduced electromagnetic interference.

It is a yet further object to provide an active and non-active coil apparatus for use of an electromagnetic method of the character indicated, wherein operation of the apparatus can proceed at reduced power levels as compared to those of related methods known in electromedicine, with attendant benefits of safety, economics, portability, and reduced electromagnetic interference and the reduced cost related to the use of the non-active coils to further disperse the treatment area.

An inductive applicator coil arrangement apparatus and method is described which allows broad spectral density bursts of electromagnetic waveforms to be applied to an active coil placed within proximity of one or more non-active coils. The non-active coils are configured to be inductively coupled to, and energized by, the active coil thereby dispersing the therapeutic output across the larger area circumscribed by the combination of active and non-active coils, to be selectively applied to a living human or animal body (or to living cells, tissues and organs) for therapeutic purposes. The active coil electromagnetic waveform output has a frequency in the range of one (1) to one hundred (100) megahertz, with one (1) to one hundred thousand (100,000) pulses per burst, and with a burst-repetition rate of one hundredth (0.01) to one thousand (1,000) Hertz. The inductive applicator coil arrangement can be placed within a mattress, pad, cushioned or non-cushioned substrate to provide application of the therapeutic output while the human or animal is lying thereupon. In addition, one or more inductive applicator coil arrangements can be placed adjacent to the tissue target by incorporating within a garment, bandage or support fabricated with compartments or sections to house the coils at appropriate anatomical locations. The inductive applicator coil arrangement may also form an integral portion of a garment designed for daily, exercise or sports use through the use of conductive thread or fine, flexible wire. The garment may be for exercise, sports, physical rehabilitation or as a post-surgical, non-invasive, non-pharmacological anti-inflammatory therapeutic modality. The inductive applicator coil arrangement may be incorporated into or be an integral part of various types of bandages, including, but not limited to, compression, elastic, cold or hot compress, etc. The waveforms applied by the active and non-active coils of the present invention were configured for maximum efficiency allowing the complete electromagnetic treatment system to be lightweight, battery operated and portable. The waveforms are designed to modulate living cell growth and repair. Particular applications of the present invention include, but are not limited to, angiogenesis, improved micro-vascular blood perfusion, vasodilation, reduced transudation, stimulation of neovascularization bone repair, wound repair, pain relief, edema reduction, increased blood flow and to provide anti-inflammatory effects.

The above and yet other objects and advantages of the present invention will become apparent from the hereinafter set forth Brief Description of the Drawings.

It is intended that any other advantages and objects of the present invention that become apparent or obvious from the detailed description, drawings or illustrations contained herein are within the scope of the present invention.

DETAILED DESCRIPTION

Figure 1:
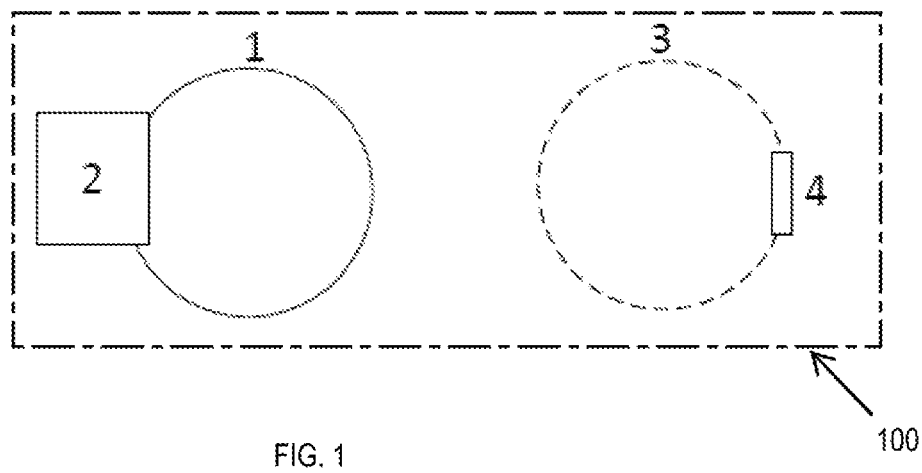
FIG. 1 is a diagram of a treatment apparatus coil array having an active coil and a non-active coil according to an exemplary embodiment of the invention.

FIG. 1 is a diagram of a treatment apparatus coil array having an active coil and a non-active coil according to an exemplary embodiment of the invention. As shown in FIG. 1, a treatment apparatus coil array 100 according to an embodiment of the invention may comprise at least one wire loop 1 forming a coil, a signal generator 2 which is powered by an electrical power supply for generating a PEMF signal to be transmitted via the coil (hereinafter also referred to as wire loop) 1 and, thereby, providing a treatment signal directed towards a human or animal subject by placing the coil 1 proximate a treatment target of the subject. Signal generator 2 may comprise drive circuitry coupled to a power source, such as a battery, a household A/C power source via a power converter, and the like.

According to an embodiment of the invention, array 100 may further comprise one or more additional coils (or wire loops), for example, coil 3 that is coupled to a tuned passive circuit 4. Circuit 4 is configured to be induced by the signal generator 2 via coils 1 and 3 to, thereby, provide a treatment signal proximate loop 3 without requiring a separate electrical power connection. Loop 3 and circuit 4 function together to output a signal based on the signal output from loop 1 and signal generator 2. In accordance with an exemplary embodiment of the invention, circuit 3 may be tuned according to the signal from loop 1 and signal generator 2 so that a treatment signal output from loop 3 is an approximate duplicate of the treatment signal output from loop 1. Consequently, an approximately uniform treatment signal field may be generated across loops 1 and 2. According to an exemplary embodiment of the invention, each coil 1 and 3 may be approximately 3 to 15 inches in diameter (e.g., AC powered apparatus), and may preferably be between 3.5 to 8.5 inches in diameter (e.g., battery powered apparatus). For example, each coil 1 and 3 may be approximately 7 inches in diameter. An optimal power output of coils 1 and 3 may be in the range of 100-300 mV (millivolts), or 110-250 mV, and is preferably an average peak-to-peak amplitude of at least 130 mV. Coils 1 and 3 forming array 100 may be mounted to a substrate, such as incorporated within a cushioned sleeve between two cushion layers that are made from, for example, foam rubber and the like. Alternatively, the coils may be embedded within a soft polymer enclosure to one side of a cushion layer. Depending upon the treatment depth needed for a patient, the treatment surface for such a treatment pad/bed may be on the polymer enclosure side or the cushion layer side. In addition, each of the coils 1 and 3 may be sized and shaped differently to accommodate differently sized arrays, pads, beds, enclosures, garments, carriers, patients, and corresponding treatment depth. As an example, a treatment pad/bed incorporating array 100 may be disposed within, for example, a pet carrier for treating small pet animals while transporting the treatment subject.

Figure 2:
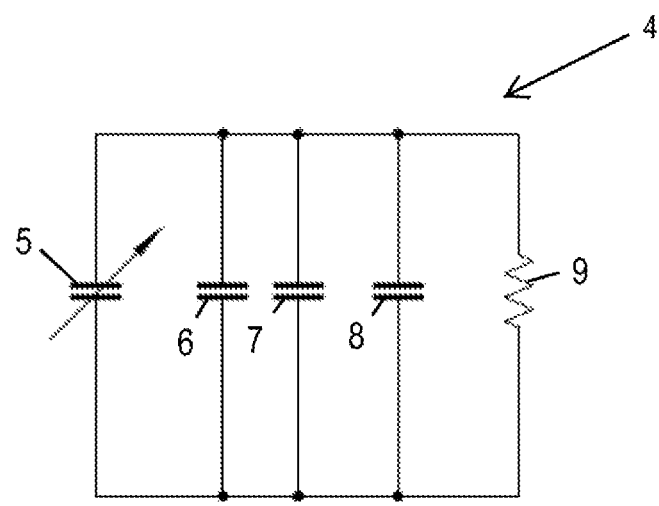
FIG. 2 is a schematic diagram of a tunable circuit for coupling to the non-active coil of FIG. 1 according to an exemplary embodiment of the invention.

FIG. 2 is a schematic diagram of tunable circuit 4 for coupling to the non-active coil 3 of FIG. 1 according to an exemplary embodiment of the invention. As shown in FIG. 2, circuit 4 may comprise one or more capacitors—for example, three (3) as illustrated in FIG. 2—connected in parallel with one or more resistors—for example, one (1) as illustrated in FIG. 2. In order to provide for the tuning according to the signal transmitted from generator 2 via coil 1, circuit 4 comprises an additional variable capacitor 5 connected in parallel to the one or more (e.g., three) capacitors 6, 7, and 8, and (e.g., one) resistors 9. As examples, the variable capacitor 5 may be a trimmer/variable capacitor with a 6.5-30 pF range at 100 V (N120), the resistor 9 may be a 15K Ohm 1% 1/10 W (0603) resistor, and the one or more capacitors 6, 7, and 8 may comprise a ceramic capacitor with 27 pF at 100 V (C0G/NP0 0603) and another ceramic capacitor with 10 pF at 100V (C0G/NP0 0603). In addition to the tuning of the variable capacitor 5, the one or more capacitors 6, 7, and 8 may be replaced with different capacitances so that the total capacitance of circuit 4 may be adjusted according to the sizes of coils 1 and 3.

Figure 3:
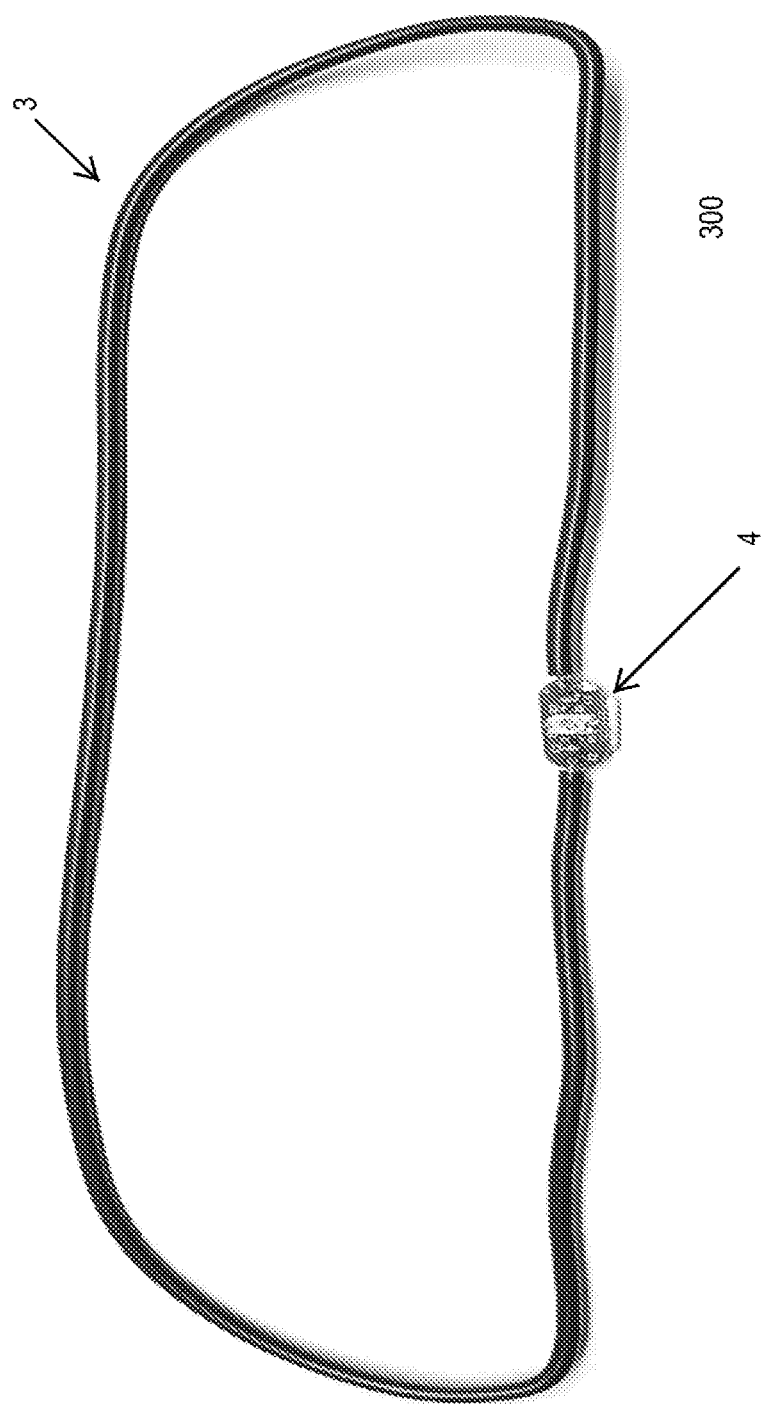
FIG. 3 is an image of a non-active coil according to an exemplary embodiment of the invention.

Again, the assembly formed by coil 3 and circuit 4 can act as both a receiver and transmitter without requiring electrical power and all the circuitry of signal generator 2. FIG. 3 is an image of non-active coil assembly 300 formed by coil 3 and circuit 4 according to an exemplary embodiment of the invention. As described above and as shown in FIG. 3, assembly 300 may comprise coil 3 that is formed in a shape that is not strictly circular—such as, for example, oval or racetrack-shaped—in order to accommodate various kinds of arrays, pads, beds, enclosures, carriers, patients, and corresponding treatment depth.

Figure 4:
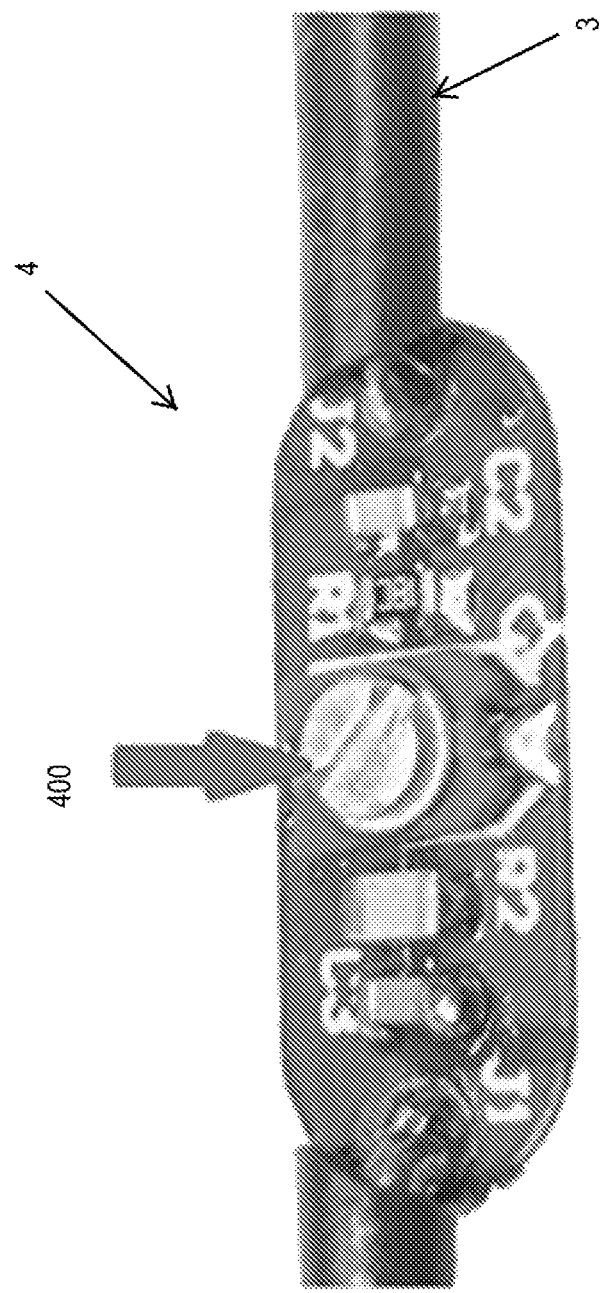
FIG. 4 is an image of a tunable circuit corresponding to the tunable circuit of FIG. 2 in accordance with an exemplary embodiment of the invention.

FIG. 4 is an image of circuit 4 connected to coil 3 and illustrating variable capacitor 400 for convenient tuning of circuit 4. According to an embodiment of the invention, circuit 4 may be disposed within an enclosure after tuning of variable capacitor 400 is completed.

Figure 5:
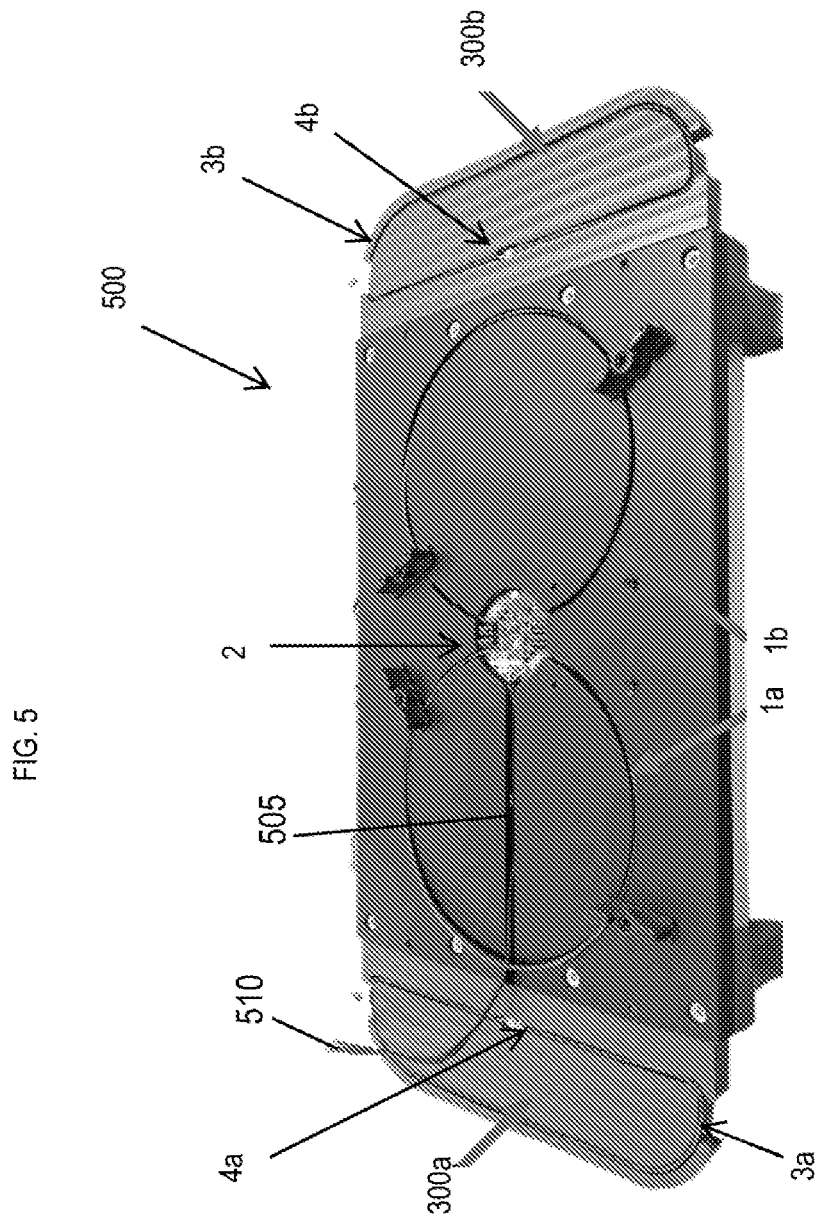
FIG. 5 is an image of a treatment apparatus coil array having two (2) active coils and two (2) non-active coils (with APB-FX001 test fixture) according to an exemplary embodiment of the invention.

FIG. 5 is an image of an array 500 having coils 1a, 1b, 3a, and 3b corresponding to coils 1 and 3, respectively, illustrated in FIG. 1 and described above. As shown in FIG. 5, coils 1a and 1b may both be connected to a same signal generator 2, which is powered by a power source through a wire 505 to a power source connector 510. According to an exemplary embodiment of the invention, different numbers of coils corresponding to coils 1a and 1b may be connected to respective signal generators—for example, coils may each be connected to a separate signal generator or plural coils having approximately the same size and shape may be connected together to a single signal generator. As further shown in FIG. 5, coils 3a and 3b may each form non-active coil assemblies 300a and 300b with respective non-active circuits 4a and 4b in correspondence with assembly 300 illustrated in FIG. 3 and described above. Correspondingly, a different number of non-active coils that are similar or different in shape and size to coils 3a and 3b may be placed in proximity of coils 1a and 1b to form array 500. For the illustrated exemplary embodiment, coils 1a and 1b have a one-to-one relationship with non-active coils 3a and 3b. According to an embodiment of the invention, coils 3a and 3b may approximate a "D" shape and may have a similar circumferential length as coils 1a and 1b, which have a diameter of approximately 7 inches. In addition, coils 1a, 1b, 3a, and 3b may have aligned centers along an axis where coil 1a and 3a (1b and 3b) are approximately 0.5 inches apart at the closest point—i.e., from the outer circumference of coil 1a/1b to circuit 4a/4b shown in FIG. 5. For testing and/or tuning purposes, array 500 may be place in a test fixture, such as the APB-FX001 Test Fixture shown in FIG. 5.

Figure 6:
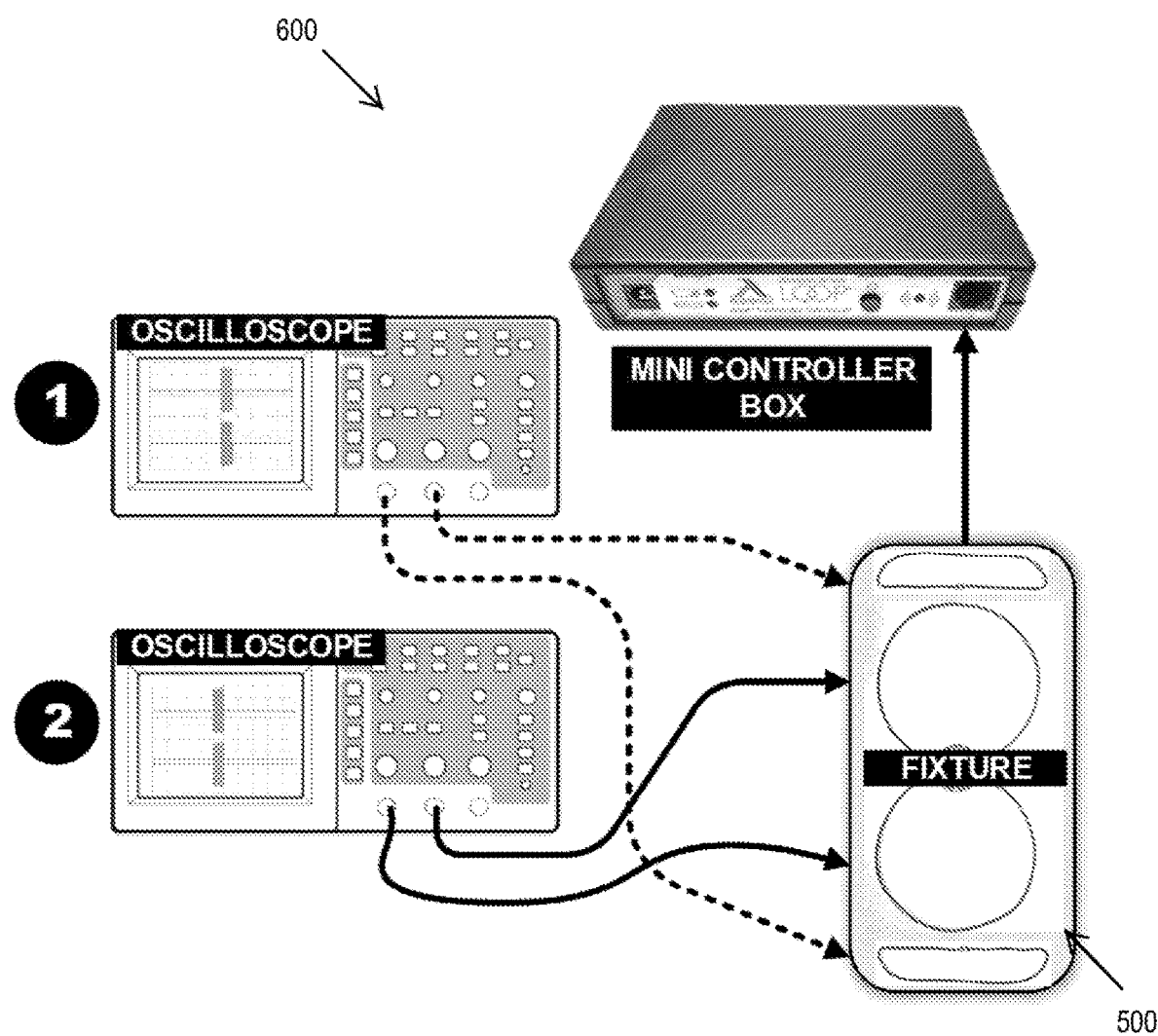
FIG. 6 is a diagram showing a testing assembly for the treatment apparatus coil array of FIG. 5 in accordance with an exemplary embodiment of the invention.

FIG. 6 is a diagram showing a testing assembly 600 for the treatment apparatus coil array 500 of FIG. 5 in accordance with an exemplary embodiment of the invention. As shown in FIG. 6, an oscilloscope (e.g., Tektronix® TDS 2012B or equivalent) with respective RF probes attached thereto (along with, for example, respective 50 Ohm Feed-through Adapters) may be used to measure the treatment signal outputs of the respective coils 1a, 1b, 3a, and 3b of array 500. For testing described below, the probes were placed at the center of the respective coils 1a, 1b, 3a, and 3b at a height of approximately 1 cm from a plane of the coils. For coils 3a and 3b, the centers, at which the probes were placed, were aligned with circuits 4a and 4b, respectively, and at an equidistance between circuits 4a and 4b and the coils 3a and 3b on the opposite sides of the respective centers. As further shown in FIG. 6, testing assembly may comprise a mini controller for controlling and adjusting the output of signal generator 2. According to an exemplary embodiment of the invention, signal generator 2 may be integrated with a controller that provides control and output functionality that corresponds to the mini controller shown in FIG. 6 for, as an example, programming array 500 in a treatment apparatus using an onboard or wireless user interface, and the like.

Figure 7A:
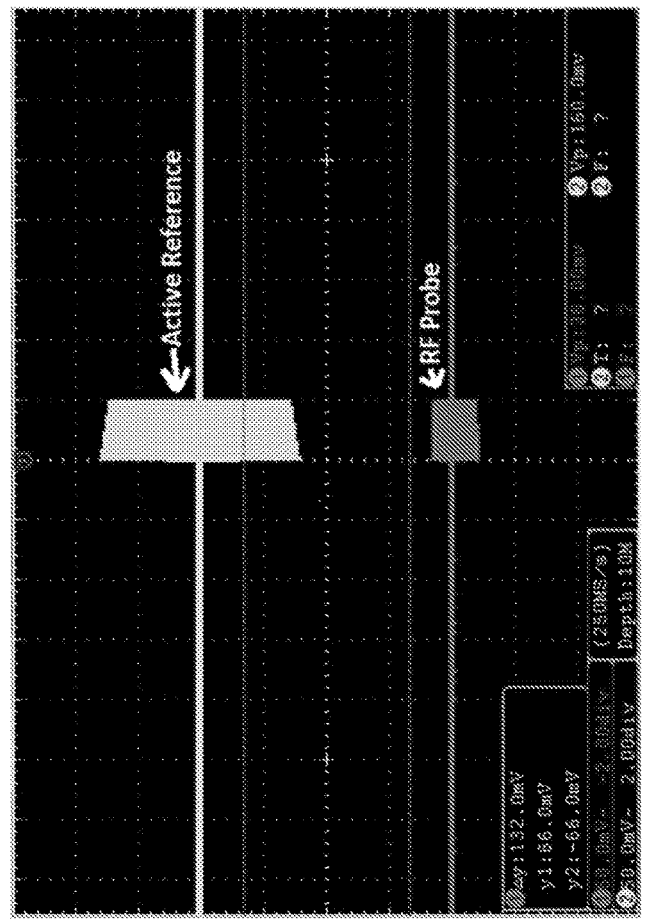
FIGS. 7A, 7B, and 7C are output diagrams showing test results from the testing assembly of FIG. 6 according to an exemplary embodiment of the invention.
Figure 7B:
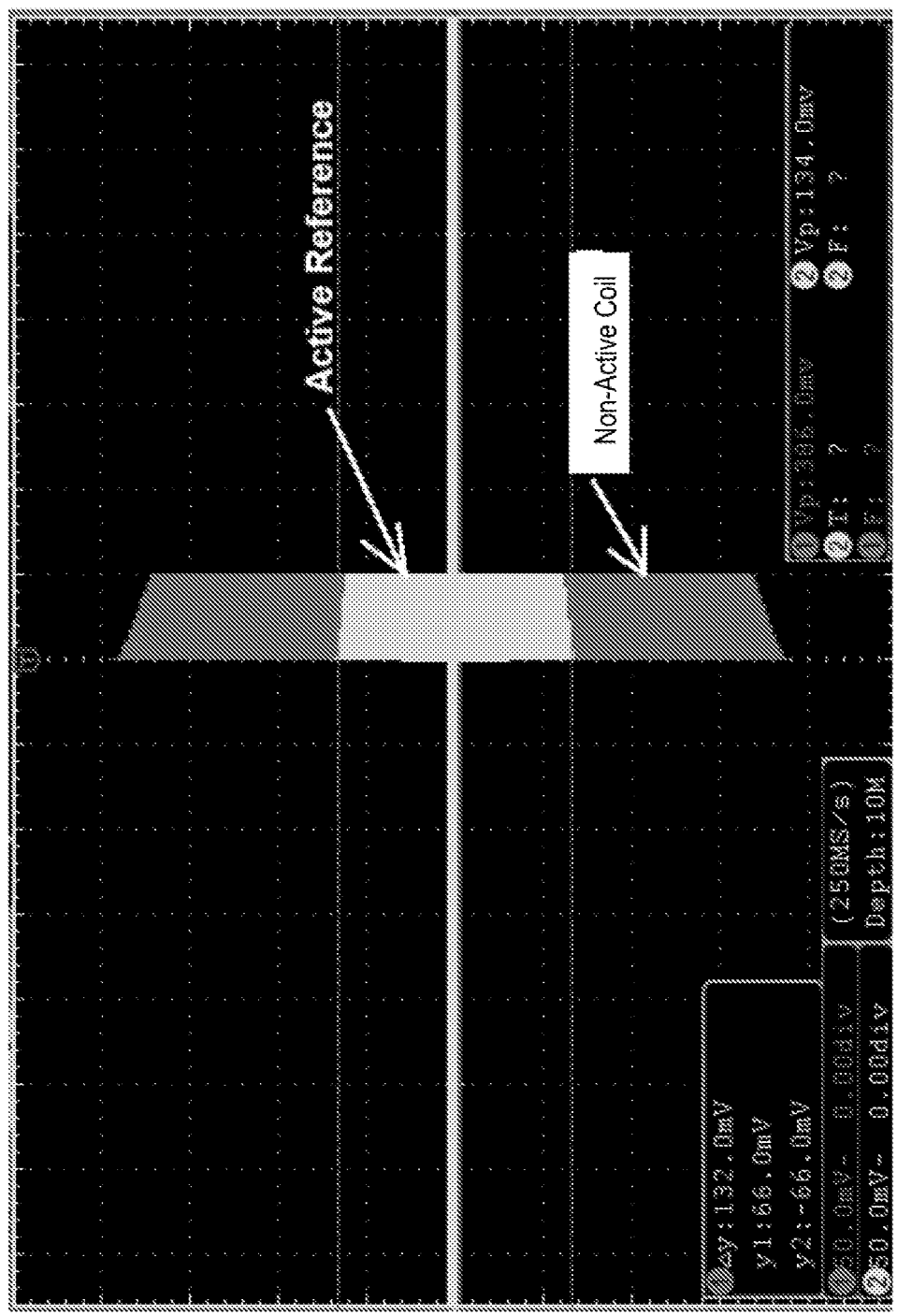
Figure 7C:
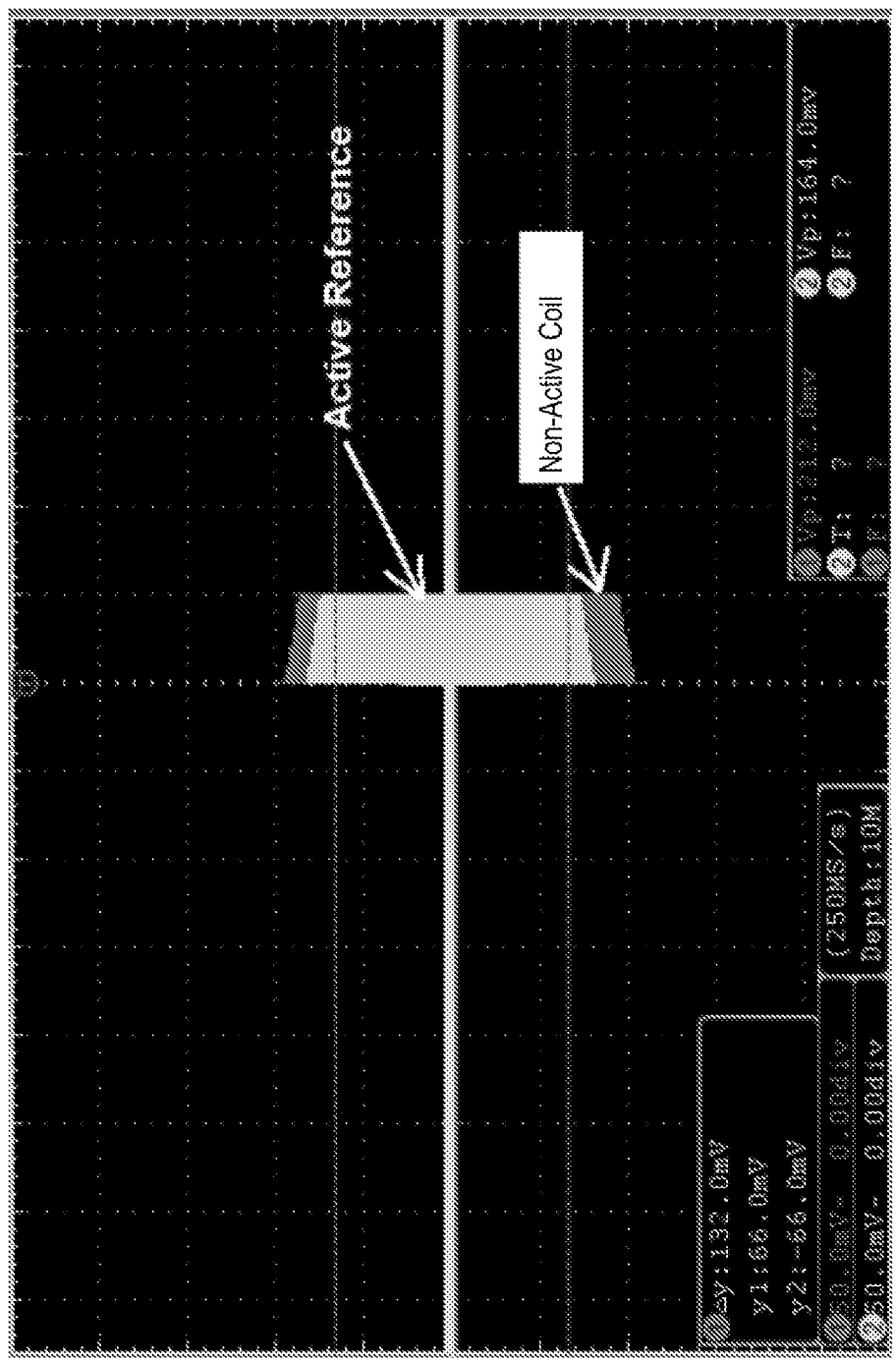

FIGS. 7A, 7B, and 7C are output diagrams of the oscilloscopes of testing assembly 600 shown FIG. 6 according to an exemplary embodiment of the invention.

In particular, FIG. 7A shows the outputs of the oscilloscopes with the RF probes placed at the center positions described above with respect to coils 1a, 1b, 3a, and 3b shown in FIG. 5 but without incorporating coils 3a and 3b in the tested array in the assembly 600 shown in FIG. 6—i.e., showing the treatment signal levels at the respective positions without incorporating non-active coil assemblies 300a and 300b. As shown in FIG. 7A, signal generator 2, as controlled by the mini controller shown in FIG. 6, causes coils 1a and 1b to produce a treatment signal with an approximate average peak-to-peak amplitude of 160 mV, which is above the desirable 130 mV level. However, the RF probes placed at the positions corresponding to coils 3a and 3b measured an average treatment signal output of only approximately 38 mV.

FIG. 7B shows the outputs of the oscilloscopes with the RF probes placed at the center positions described above with respect to coils 1a, 1b, 3a, and 3b shown in FIG. 5 and incorporating coils 3a and 3b in the tested array in the assembly 600 shown in FIG. 6 but without tuning non-active coil assemblies 300a and 300b to the signals output from signal generator 2 and coils 1a and 1b. As shown in FIG. 7B, signal generator 2, as controlled by the mini controller shown in FIG. 6 and which corresponds to the signal input for FIG. 7A, causes coils 1a and 1b to produce a treatment signal with an approximate average peak-to-peak amplitude of 134 mV, which is above the desirable 130 mV level. However, the RF probes placed at the positions corresponding to coils 3a and 3b measured an average treatment signal output of approximately 386 mV. This un-tuned signal profile across array 500 reflects an undesirable non-uniform treatment signal field (i.e., resulting in a less than optimal treatment field for the array), which may also result in undue power drain from the electric energy source (such as a battery) for signal generator 2.

FIG. 7C shows the outputs of the oscilloscopes with the RF probes placed at the center positions described above with respect to coils 1a, 1b, 3a, and 3b shown in FIG. 5 and incorporating coils 3a and 3b in the tested array in the assembly 600 shown in FIG. 6 and with non-active coil assemblies 300a and 300b—i.e., their respective circuit 4—being tuned to the signals output from signal generator 2 and coils 1a and 1b. As shown in FIG. 7C, signal generator 2, as controlled by the mini controller shown in FIG. 6 and which corresponds to the signal input for FIGS. 7A and 7B, causes coils 1a and 1b to produce a treatment signal with an approximate average peak-to-peak amplitude of 164 mV, which is above the desirable 130 mV level. In addition, the RF probes placed at the positions corresponding to coils 3a and 3b measured an average treatment signal output of approximately 212 mV. In other words, the tuned signal profile across array 500 provided a more uniform treatment signal field that is consistently above the desirable 130 mV level. According to an exemplary embodiment of the invention, the variable capacitors of the circuits 4a and 4b may be tuned such that the measured outputs of the coils 1a/1b and 3a/3b, as described above, are within a 5%-40% range of each other, or preferably within a 5%-20% range of each other, or more preferably within a 5%-15% range of each other.

As a result, with appropriate tuning, one or more non-active coil assemblies corresponding to assembly 300 (300a and 300b) shown and described above may be placed in the vicinity of one or more "active" coils—corresponding to coils 1a and 1b shown and described above—in order to extend a uniform treatment signal field, for example, to form irregularly shaped treatment pads, beds, enclosures, garments, and the like, without requiring undue additional power from the power source. As described above, an array according to the invention may incorporate any number of active and non-active coils of various sizes and shapes based on the size, shape, treatment depth, etc. of the array and corresponding treatment subject.

Based on the above-described tuning, a device as described herein can be configured so that it applies a bio-effective waveform for a predetermined amount of time using a predetermined (or modifiable) treatment regime. In one variation, the signal frequency within a particular burst envelope is centered on a particular carrier frequency (e.g., 27.12 MHz, 6.78 MHz, etc.). For example, the waveform within a burst may use a carrier frequency of 6.78 MHz and the frequency between bursts can be modulated by producing bursts at 1 Hz. In one variation, bursts are 7 ms in duration with a peak amplitude of 0.05 Gauss. In another example, a device can be configured using a carrier frequency of 27.12 MHz that can be modulated by producing a burst at 2 Hz, such bursts being 2 ms in duration with a peak amplitude of 0.05 Gauss. In some variations, the device is configured to explicitly limit the peak signal strength of the applied signal. For example, the peak signal strength may be limited to approximately 50 milliGauss (e.g., 0.05 Gauss). A proper signal configuration to produce the necessary induced electric fields in the range of 0.1-100 millivolts per centimeter ("mV/cm") for a given carrier frequency may be determined as described herein. In general, the desired and specific effect seen on the target pathway (e.g., the Ca/CaM pathway) may be very sensitive to the waveform parameters. The ranges of waveform parameters described herein are tuned to the desired effect.

Example 1

Figure 8A:
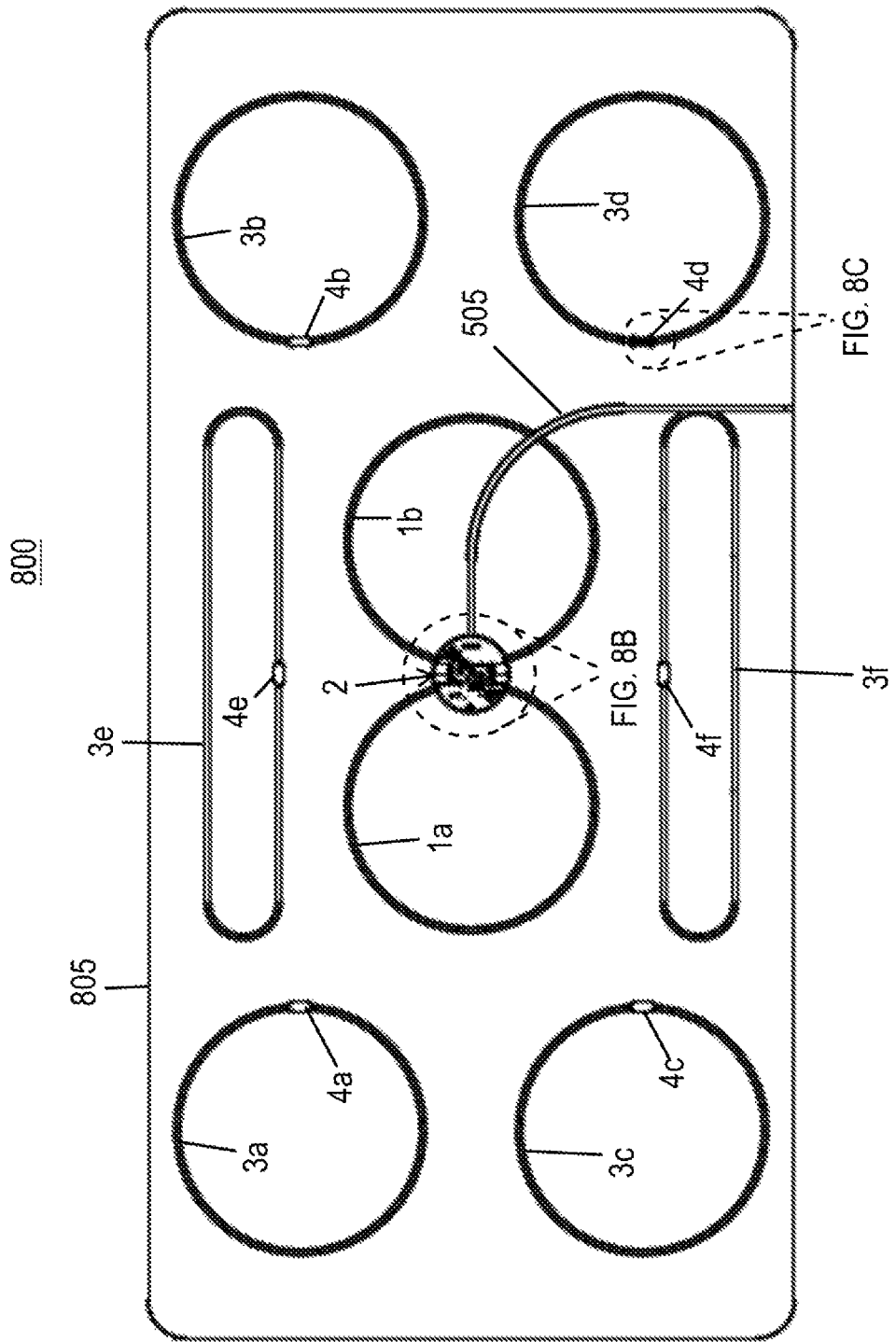
FIG. 8A is a diagram illustrating a coil array for a treatment apparatus having two (2) active coils and six (6) non-active coils according to an exemplary embodiment of the invention.

FIG. 8A is a diagram of an array 800 having two (2) active coils 1a and 1b, and six (6) non-active coils 3a, 3b, 3c, 3d, 3e, and 3f that correspond to coils 1 and 3, respectively, illustrated in FIG. 1 and described above, the coils 1a, 1b, and 3a-3f, together with circuits 2 and 4a-4f being disposed in a substrate 805. As shown in FIG. 8A, coils 1a and 1b are both connected to a same signal generator 2, which is powered by a power source through a wire 505. In embodiments, different numbers of coils corresponding to coils 1a and 1b may be connected to respective signal generators— for example, coils may each be connected to a separate signal generator or plural coils having approximately the same size and shape may be connected together to a single signal generator.

Figure 8B:
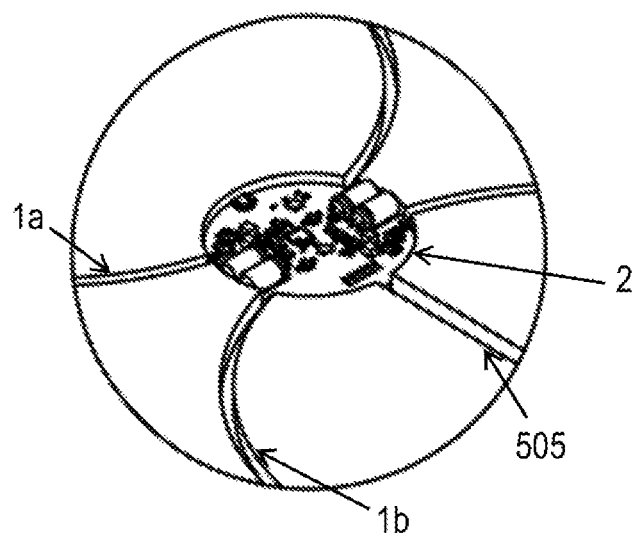
FIG. 8B is a closeup view of a signal generator coupled to the active coils in the coil array shown in FIG. 8A.

As illustrated in FIG. 8A, coils 1a and 1b are connected to and positioned to either side of signal generator 2, a closeup view of which is shown in FIG. 8B. Signal generator 2 is coupled to a power source (not shown), such as a battery, a household A/C power source via a power converter, and the like, through wire 505. Signal generator 2 includes two (2) drive circuitry units each with control functionality and may be coupled, individually or collectively, to another control device (not shown), such as a general-purpose computing device. The control device may provide instructions for signal generation by the drive circuitry units in signal generator 2 via the coils 1a and 1b. Each of the two (2) drive circuitry units in signal generator 2 includes a tuning element that is a circuit used to adjust and match an impedance of a PEMF short wave radio frequency generator to an emitter applicator—i.e., a corresponding one of the coils 1a and 1b—post assembly. The post assembly impedance adjustments compensate for variability in standard components to optimize radio frequency power output while conforming with ISM bandwidth regulations. FDA-cleared PEMF devices use 27.12 MHz as the standard carrier frequency. The tuning elements each include, for connecting to respective ones of coils 1a and 1b, a 15 kΩ resistor, a 6 pF capacitor, a 27 pF capacitor, and two (2) variable 2-10 pF capacitors connected in parallel for operational tuning.

As further shown in FIG. 8A, non-active coils 3a, 3b, 3c, 3d, 3e, and 3f each form non-active coil assemblies in correspondence with assembly 300 with respective non-active circuits 4a, 4b, 4c, 4d, 4e, and 4f in correspondence with circuit 4 illustrated in FIG. 3 and described above. Correspondingly, in embodiments, a different number of non-active coils that are similar or different in shape and size to coils 3a-3f may be placed in proximity of coils 1a and 1b to form array 800. As illustrated in FIG. 8A, the number of coils 1a and 1b have a general one-to-three relationship with the number of non-active coils 3a-3f. Coils 3a-3d have circular shapes of similar dimensions to active coils 1a and 1b, and coils 3e and 3f have oval shapes, with two axes of symmetry (i.e., racetrack shape), and have end-to-end lengths that equal approximately a corresponding end-to-end length of the coils 1a and 1b, each of which having a diameter of approximately 5.5 inches, connected side-by-side through signal generator 2. The measured diameters of circular coils 1a-1b and 3a-3d equaled 5.5 inches and the measured dimensions of oval coils 3e and 3f were 2 inches width by 14 inches length. It was determined through experimentation that desirable dimensions of oval-shaped non-active coils, such as coils 3e and 3f, would approximate an area coverage that is equivalent to a circular area with a 7 inch to 8.5 inch diameter. It was further determined through experimentation that desirable distances among the coils would be between 0.25 to 3 inches, preferably between 0.5 to 2 inches. The resulting substrate 805, made from a flexible material, measured 35 inches long and 17 inches wide.

Figure 8C:
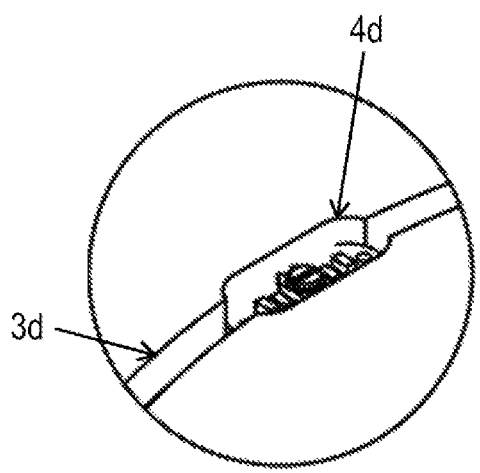
FIG. 8C is a closeup view of a tunable non-active circuit coupled to a non-active coil in the coil array shown in FIG. 8A.

FIG. 8C is a closeup view of non-active circuit 4d, which includes the following parameters for components corresponding to those described above with respect to circuit 4 shown in FIG. 2: a 2 pF capacitor, a 56 pF capacitor, and a 2-10 pF variable capacitor connected in parallel for operational tuning with active coils 1a and 1b and the circuit units in signal generator 2. Non-active circuits 4a, 4b, and 4c have the same corresponding tuning components. Circuits 4e and 4f for oval-shaped loops 3e and 3f have parameters that correspond to those of circuits 4a-4h illustrated in FIGS. 9A and 9B and described in further detail below for EXAMPLE 2.

As shown in FIG. 8A, circuits 4a-4f are disposed in substrate 805 on sides of non-active coils 3a-3f, respectively, towards active coils 1a and 1b. Signal generator 2 generates the above-described treatment signals—i.e., signals with a carrier frequency of 27.12 MHz that are modulated by producing a burst at 2 Hz, such bursts being 2 ms in duration with a peak amplitude of 0.05 Gauss—either simultaneously or sequentially via active coils 1a and 1b.

Example 2

Figure 9A:
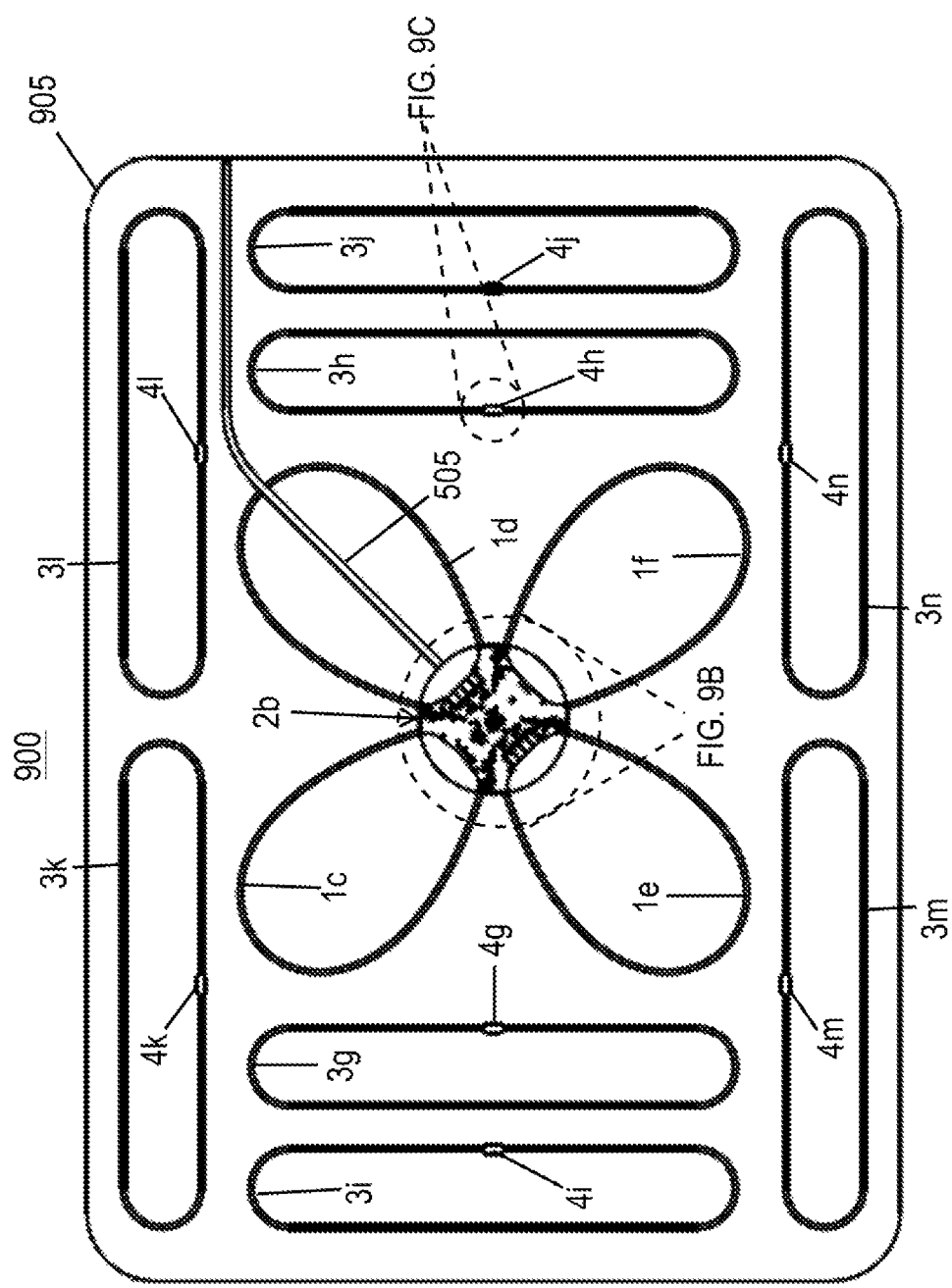
FIG. 9A is a diagram illustrating a coil array for a treatment apparatus having four (4) active coils and eight (8) non-active coils according to an exemplary embodiment of the invention.

FIG. 9A is a diagram of an array 900 having four (4) active coils 1c, 1d, 1e, and 1f, and eight (8) non-active coils 3g, 3h, 3i, 3j, 3k, 3l, 3m, and 3n that correspond to coils 1 and 3, respectively, illustrated in FIG. 1 and described above, the coils 1c-1f, and 3g-3n, together with circuits 2b and 4g-4n being disposed in a substrate 905. As shown in FIG. 9A, coils 1c-1f are all connected to a same signal generator 2b, which is powered by a power source through a wire 505. In embodiments, different numbers of coils corresponding to coils 1c-1f may be connected to respective signal generators—for example, coils may each be connected to a separate signal generator or plural coils having approximately the same size and shape may be connected together to a single signal generator.

Figure 9B:
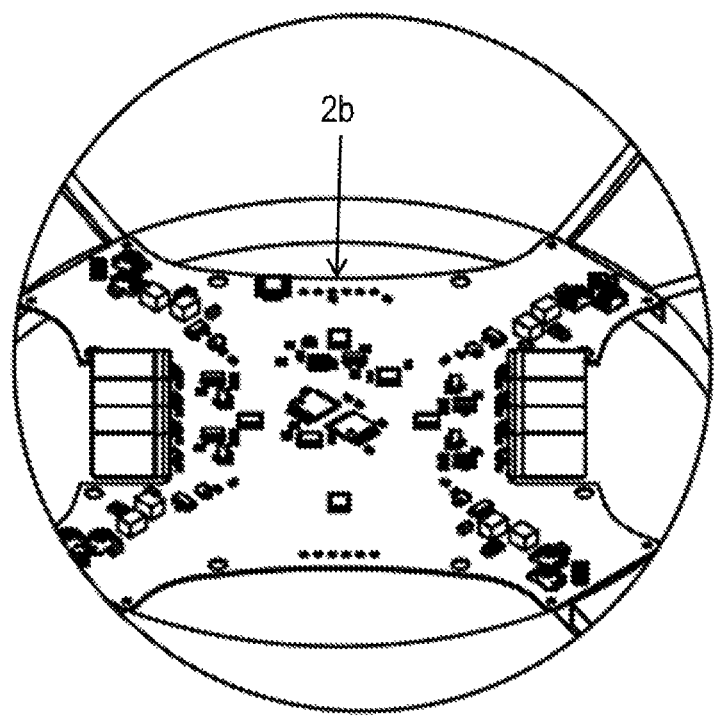
FIG. 9B is a closeup view of a signal generator coupled to the active coils in the coil array shown in FIG. 9A.

As illustrated in FIG. 9A, coils 1c-1f having oval shapes, with one axis of symmetry (i.e. egg shape), are connected to and positioned at respective sides of signal generator 2b, a closeup view of which is shown in FIG. 9B, forming substantially a clover arrangement around signal generator 2b. Signal generator 2b is coupled to a power source (not shown), such as a battery, a household A/C power source via a power converter, and the like, through wire 505. Signal generator 2b includes four (4) drive circuitry units each with control functionality and may be coupled, individually or collectively, to another control device (not shown), such as a general-purpose computing device. The control device may provide instructions for signal generation by the drive circuitry units in signal generator 2b via the coils 1c-1f. Each of the four (4) drive circuitry units in signal generator 2b includes a tuning element that is a circuit used to adjust and match an impedance of a PEMF short wave radio frequency generator to an emitter applicator—i.e., a corresponding one of the coils 1c-1f—post assembly. The post assembly impedance adjustments compensate for variability in standard components to optimize radio frequency power output while conforming with ISM bandwidth regulations. FDA-cleared PEMF devices use 27.12 MHz as the standard carrier frequency. The tuning elements each include, for connecting to respective ones of coils 1c-1f, a 10 pF capacitor, a 27 pF capacitor, and two (2) variable 2-10 pF capacitors connected in parallel for operational tuning.

As further shown in FIG. 9A, non-active coils 3g, 3h, 3i, 3j, 3k, 3l, 3m, and 3n each form non-active coil assemblies in correspondence with assembly 300 with respective non-active circuits 4g, 4h, 4i, 4j, 4k, 4l, 4m, and 4n in correspondence with circuit 4 illustrated in FIG. 3 and described above. Correspondingly, in embodiments, a different number of non-active coils that are similar or different in shape and size to coils 3g-3n may be placed in proximity of coils 1c-1f to form array 900. As illustrated in FIG. 9A, the number of coils 1c-1f have a general one-to-two relationship with the number of non-active coils 3g-3n. Coils 3g-3n have oval shapes, with two axes of symmetry (i.e., racetrack shape). Active coils 1c-1f have a longer diameter dimension of approximately 7 inches and a shorter diameter dimension of approximately 5 inches at a widest point and 2.75 inches at the respective couplings to signal generator 2b. The measured dimensions of oval non-active coils 3g-3n were 2 inches width by 14.5 inches length. Again, it was determined through experimentation that desirable dimensions of oval-shaped non-active coils, such as coils 3g-3n, would approximate an area coverage that is equivalent to a circular area with a 7 inch to 8.5 inch diameter. It was further determined through experimentation that desirable distances among the coils would be between 0.25 to 3 inches, preferably between 0.5 to 2 inches. The resulting substrate 905, made from a flexible material, measured 32.5 inches long and 23.5 inches wide.

Figure 9C:
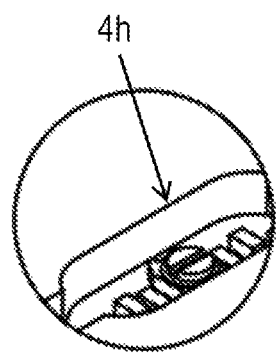
FIG. 9C is a closeup view of a tunable non-active circuit coupled to a non-active coil in the coil array shown in FIG. 9A.

FIG. 9C is a closeup view of non-active circuit 4h, which includes the following parameters for components corresponding to those described above with respect to circuit 4 shown in FIG. 2: a 43 pF capacitor and a 2-10 pF variable capacitor connected in parallel for operational tuning with active coils 1c-1f and the circuit units in signal generator 2b. Non-active circuits 4g, 4i, 4j, 4k, 4l, 4m, and 4n have the same corresponding tuning components.

As shown in FIG. 9A, circuits 4g-4n are disposed in substrate 905 on sides of non-active coils 3g-3n, respectively, towards active coils 1c-1f. Signal generator 2b generates the above-described treatment signals—i.e., signals with a carrier frequency of 27.12 MHz that are modulated by producing a burst at 2 Hz, such bursts being 2 ms in duration with a peak amplitude of 0.05 Gauss—either simultaneously or sequentially via active coils 1c, 1d, 1e, and 1f.

While particular embodiments of the present invention have been shown and described in detail, it would be obvious to those skilled in the art that various modifications and improvements thereon may be made without departing from the spirit and scope of the invention. It is therefore intended to cover in the appended claims all such modifications and improvements that are within the scope of this invention.

The invention claimed is:

1. An apparatus for providing pulsed electromagnetic field (PEMF) treatment, comprising:
    a substrate;
    one or more first electrically-conductive loops on the substrate connected to one or more corresponding signal generators configured to generate one or more PEMF signals at the one or more first electrically-conductive loops;
    one or more second electrically-conductive loops each connected to a respective tunable non-active circuit, the one or more second electrically-conductive loops being arranged at a predetermined inductive coupling compatible distance from the one or more first electrically-conductive loops on the substrate to form an array,
    wherein each tunable non-active circuit comprises at least one variable capacitor for tuning each of the one or more second electrically-conductive loops to the one or more PEMF signals.

2. The apparatus of claim 1, wherein each of the first and second electrically-conductive loops has a diameter of between approximately 4 inches and 8 inches.

3. The apparatus of claim 1, wherein the one or more first electrically-conductive loops comprise two first electrically-conductive loops connected to two corresponding signal generators and the one or more second electrically-conductive loops comprise a plurality of second electrically-conductive loops connected to respective tunable non-active circuits.

4. The apparatus of claim 3, wherein the two corresponding signal generators simultaneously transmit respective radio frequency signals via the two first electrically-conductive loops.

5. The apparatus of claim 3, wherein the two corresponding signal generators transmit respective radio frequency signals consecutively via the two first electrically-conductive loops.

6. The apparatus of claim 1, wherein the one or more first electrically-conductive loops comprise four first electrically-conductive loops connected to four corresponding signal generators and the one or more second electrically-conductive loops comprise four or more second electrically-conductive loops connected to respective tunable non-active circuits.

7. The apparatus of claim 6, wherein the four corresponding signal generators simultaneously transmit respective radio frequency signals via the four first electrically-conductive loops.

8. The apparatus of claim 6, wherein the four corresponding signal generators transmit respective radio frequency signals consecutively via the four first electrically-conductive loops.

9. The apparatus of claim 1, wherein the substrate comprises a flexible material.

10. An apparatus for treating a subject by applying one or more pulsed electromagnetic field (PEMF) signals, comprising:
    one or more generator circuits each configured to generate a radio frequency (RF) signal;
    an array of plural loop antennas, at least one of the plural loop antennas being coupled to one of the one or more generator circuits and at least another one of the plural loop antennas being coupled to a respective tunable non-active circuit, each loop antenna comprising a conductor coil; and
    a substrate configured to mount at least the array of plural loop antennas, said substrate and the array of plural loop antennas forming a treatment surface configured to be disposed proximate the subject,
    wherein each tunable non-active circuit comprises at least one variable capacitor for tuning the respective tunable non-active circuit to the RF signal generated by the one or more generator circuits.

11. The apparatus of claim 10, wherein each loop antenna coil has a diameter of between approximately 4 inches and 8 inches.

12. The apparatus of claim 10, wherein the one or more generator circuits comprise two generator circuits coupled to respective two loop antennas, and the at least another one of the plural loop antennas comprises a plurality of loop antennas coupled to respective tunable non-active circuits.

13. The apparatus of claim 12, wherein the two generator circuits simultaneously transmit respective radio frequency signals via the respective two loop antennas.

14. The apparatus of claim 12, wherein the two generator circuits transmit respective radio frequency signals consecutively via the respective two loop antennas.

15. The apparatus of claim 10, wherein the one or more generator circuits comprise four generator circuits coupled to respective four loop antennas, and the at least another one of the plural loop antennas comprises four or more loop antennas coupled to respective tunable non-active circuits.

16. The apparatus of claim 15, wherein the four generator circuits simultaneously transmit respective radio frequency signals via the respective four loop antennas.

17. The apparatus of claim 15, wherein the four generator circuits transmit respective radio frequency signals consecutively via the respective four loop antennas.

18. The apparatus of claim 10, wherein the substrate comprises a flexible material.

19. A method for treating a subject by applying one or more pulsed electromagnetic field (PEMF) treatment signals, comprising:
  providing an array of a plurality of loop antennas, at least one of which is coupled to a corresponding one or more generator circuits on a substrate configured to mount at least the array of the plurality of loop antennas, said substrate comprising a treatment surface configured to be placed proximate the subject; and
  activating the one or more generator circuits to generate the one or more PEMF treatment signals to the corresponding one or more of the plurality of loop antennas, wherein the array of the plurality of loop antennas comprises at least one loop antenna connected to a tunable non-active circuit having at least one variable capacitor for tuning the respective tunable non-active circuit to the one or more PEMF treatment signals generated by the one or more generator circuits; and
  wherein the at least one loop antenna connected to the tunable non-active circuit is separate from and functionally distinct than the at least one loop antenna coupled to the one or more generator circuits.

20. A method of manufacturing an apparatus for treating a subject by applying one or more pulsed electromagnetic field (PEMF) signals, comprising:
  coupling one or more first loop antennas to a corresponding one or more generator circuits;
  placing one or more second loop antennas, each connected to a tunable non-active circuit comprising at least one variable capacitor, at a predetermined inductive coupling compatible distance from the one or more first loop antennas to form an array;
  tuning each tunable non-active circuit by adjusting the respective at least one variable capacitor according to a detected output from the one or more generator circuits; and
  providing a substrate for mounting the array.

* * * * *